United States Patent
Paik et al.

(10) Patent No.: US 9,851,336 B2
(45) Date of Patent: Dec. 26, 2017

(54) GAS SENSOR PACKAGE

(71) Applicant: LG INNOTEK CO., LTD., Seoul (KR)

(72) Inventors: Jee Heum Paik, Seoul (KR); Ji Hun Hwang, Seoul (KR)

(73) Assignee: LG INNOTEK CO., LTD., Seoul (KR)

( * ) Notice: Subject to any disclaimer, the term of this patent is extended or adjusted under 35 U.S.C. 154(b) by 216 days.

(21) Appl. No.: 14/486,450

(22) Filed: Sep. 15, 2014

(65) Prior Publication Data

US 2015/0075258 A1 Mar. 19, 2015

(30) Foreign Application Priority Data

Sep. 16, 2013 (KR) .......................... 10-2013-0111260
Jan. 10, 2014 (KR) .......................... 10-2014-0003257

(51) Int. Cl.
*G01N 7/00* (2006.01)
*G01N 33/00* (2006.01)
*G01N 27/04* (2006.01)

(52) U.S. Cl.
CPC ....... *G01N 33/0027* (2013.01); *G01N 27/041* (2013.01)

(58) Field of Classification Search
CPC .... G01N 27/04; G01N 27/041; G01N 27/123; G01N 33/0004; G01N 33/0009; G01N 33/0027
USPC ..... 73/31.05, 31.06; 204/424, 425, 428, 431
See application file for complete search history.

(56) References Cited

U.S. PATENT DOCUMENTS

| 6,140,144 | A | * | 10/2000 | Najafi | B81C 1/00269 |
| | | | | | 438/106 |
| 2007/0107493 | A1 | * | 5/2007 | Katsuda | G01N 33/0009 |
| | | | | | 73/23.31 |
| 2010/0230297 | A1 | * | 9/2010 | Wahl | B65D 1/0215 |
| | | | | | 205/781 |
| 2015/0075257 | A1 | * | 3/2015 | Paik | G01N 33/0042 |
| | | | | | 73/31.05 |
| 2015/0090002 | A1 | * | 4/2015 | Paik | B81B 7/0061 |
| | | | | | 73/31.06 |
| 2015/0198551 | A1 | * | 7/2015 | Jun | H01L 23/3107 |
| | | | | | 204/431 |

* cited by examiner

*Primary Examiner* — Benjamin Schmitt
(74) *Attorney, Agent, or Firm* — KED & Associates, LLP (57) ABSTRACT

A gas sensor package is configured such that an output change part is provided in the gas sensor package including a gas sensor so that a resistance output mode can be changed to a voltage output mode, thereby enabling the gas sensor to have a regular initial voltage value by compensating a resistance change value to an initial gas sensing material. According to embodiments of the present application, a gas sensor package is configured such that a gas moving separation part is formed between a gas sensing element and a substrate with regard to a structure in which a gas sensing element is mounted to the substrate in a flip chip bonding method so that gas can be smoothly moved and thus gas sensing efficiency can be maximized.

14 Claims, 8 Drawing Sheets

GAS SENSOR PACKAGE

CROSS-REFERENCE TO RELATED APPLICATIONS

This application claims priority to Korean Patent Application Nos. 10-2013-0111260, filed on Sep. 16, 2013, and 10-2014-0003257, filed on Jan. 10, 2014, in the Korean Intellectual Property Office, the entire contents of which are hereby incorporated by reference.

BACKGROUND

1. Field

The present application relates to a gas sensor package.

2. Background

With regard to requirements required for a gas sensor, the gas sensor is needed to have characteristics, such as speed showing how fast the gas sensor can respond to a situation, sensibility which can respond to the detection of gas in spite of the detection of a small amount of the gas, durability showing how long the gas sensor can operate, economic efficiency showing that the sensor can be used by consumers without burdens, and the like. In order for the gas sensor to be combined with an existing semiconductor process technology, the gas sensor should have characteristics of the easiness of integration and enumeration. A home gas leakage alarm made of tin oxide ($SnO_2$) as a material and the like come into wide use as a practical gas sensor. With regard to an operation principle thereof, the gas sensor is divided into a semiconductor type using a change of resistance values according to a change in the amount of gas and an oscillator type using a change in an oscillation frequency generated when gas is absorbed onto an oscillator, which oscillates with a predetermined frequency. Most of the gas sensors have been used as the semiconductor type having simple circuits and showing a stable thermal property at room temperature.

In order for the gas sensor to be applied to IT devices by packaging the gas sensor, analog output (resistance output) mode should be changed into a digital output (voltage output) mode. To do so, resistance, which is similar to or equal to a resistance value, should be applied to a sensing material of the gas sensor, and thus the resistance of an end of the sensing material should be changed into a voltage. However, the sensing material is problematic in that sensing efficiency is reduced because a resistance value of the basic material is changed according to a temperature, and thus an initial resistance value is not regular.

Furthermore, a gas sensor has a package structure in which a gas sensing material or a sensing chip is mounted to the gas sensor. According to the general gas sensor, a separate cap member for protecting an upper surface of the gas sensing material or the sensing chip is provided, and a mesh-shaped member formed of minute nets is provided on an upper surface of the cap member so as to allow the ventilation of gas.

In this gas sensing package for sensing gas, a height of an upper structure is increased due to the cap member and the mesh-shaped member, and an entire size of the gas sensing package is further increased up to several times to dozens of times than that of a sensor chip because a wire bonding method is used when the sensor chip is connected to an electrode part. Due to this problem, there is a limit to implement miniaturization of the gas sensor.

BRIEF DESCRIPTION OF THE DRAWINGS

The embodiments will be described in detail with reference to the following drawings in which like reference numerals refer to like elements wherein.

DETAILED DESCRIPTION OF THE INVENTION

Figure 1:
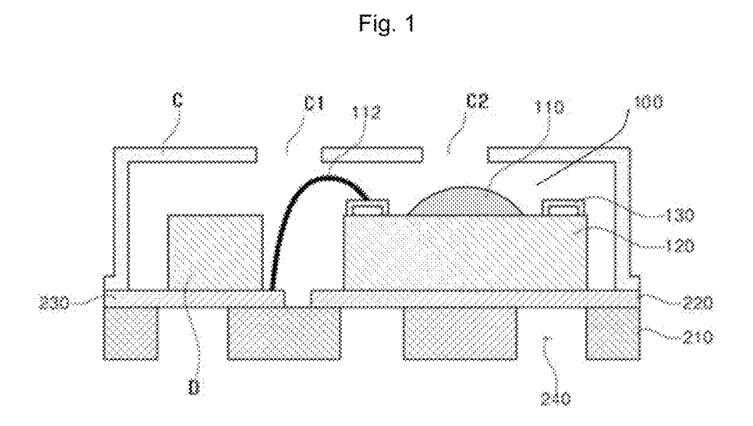
FIG. 1 illustrates a sectional view of the configuration of a gas sensor package according to an embodiment of the present application.
Figure 2:
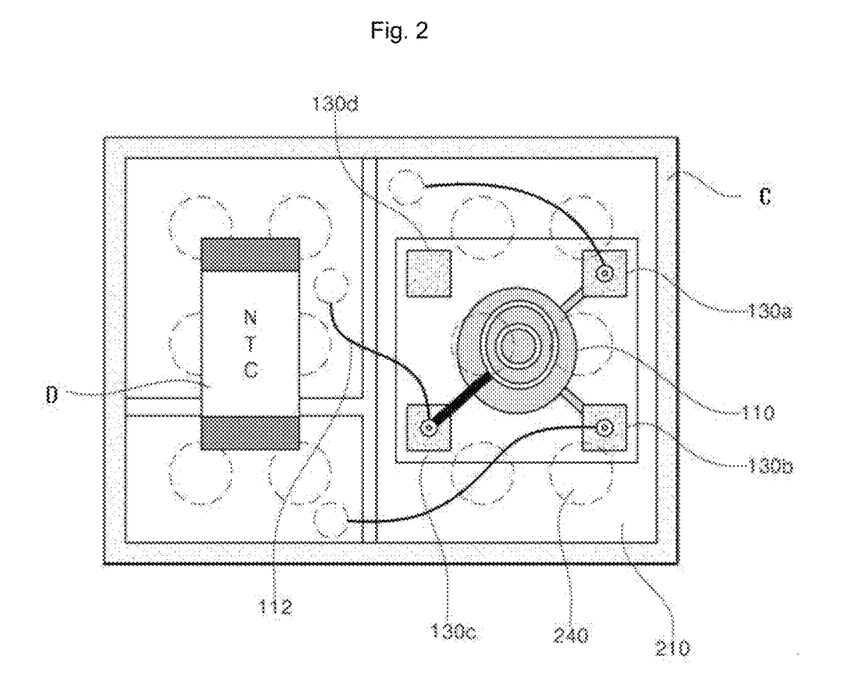
FIG. 2 illustrates a planar view of the configuration of the gas sensor package according to the embodiment of the present application.

FIG. 1 illustrates a sectional view of the configuration of a gas sensor package according to an embodiment of the present application. Also, FIG. 2 illustrates a planar view of the configuration of the gas sensor package according to the embodiment of the present application;

Referring to FIGS. 1 and 2, a gas sensor package according to the present embodiment may include a first substrate 210 including a plurality of metal patterns 220; a gas sensing element 100 mounted to the first substrate 210; and an output change part D mounted to the first substrate 210 and configured for changing an output mode of the gas sensing element 100.

The first substrate 210 is formed in a structure in which a plurality of metal patterns 220, 230 patterned with electrode patterns (circuit patterns) with a metal material is included on a surface of the first substrate made of an insulating material. The gas sensing element 100 is mounted on the metal pattern 220 and is bonded to peripheral electrodes via a wire 112. A bonding structure of the wire 112 shows an example of an electrical connection with the gas sensing element 100. It is apparent to one of ordinary skill in the art that various other bonding methods may be used, e.g., a flip chip bonding method.

A characteristic element of the present application is that an output change part D including an output change element for performing an output change function is mounted on the metal pattern 230 so as to be electrically connected to the gas sensing element 100. The output change part D may include a passive element for converting the output of a resistance mode to the output of a voltage mode, and a fixed resistance or negative temperature coefficient (NTC) thermistor electrically connected to the metal pattern and the gas sensing element may be applied as the passive element.

The output change part may be applied to various IT devices (including smart phones) by changing and packaging a resistance output mode of the gas sensing element into a voltage output mode. A fixed resistance or negative temperature coefficient (NTC) thermistor is attached to the side of an end of the gas sensing element so that the resistance mode can be converted into the voltage output mode.

As illustrated in FIG. 1, when the negative temperature coefficient (NTC) thermistor is connected to the side of the end of the gas sensing element, it is advantageous in that the gas sensor may have a regular initial voltage value by compensating a resistance change value to an initial gas sensing material according to each temperature.

In a general gas sensor package, a resistance output signal is changed into a voltage output signal using external resistance of the gas sensor package. However, when a resistance or negative temperature coefficient (NTC) thermistor is used in the outside of a printed circuit board, it is problematic in that an entire size of a module is increased, and a separate circuit design may be needed. The present application may provide a gas sensor miniaturized by implementing the gas sensor package including the output change part capable of converting the output of the gas sensor into a voltage in an inner portion of the package.

When a resistance change value for each temperature is adopted in the negative temperature coefficient (NTC) thermistor in the same ratio as that of a resistance curve to the sensing material, temperature compensation may be performed, thereby enabling the compensation of resistance according to a change in temperature to the initial sensing material.

Referring to FIG. 2, an appropriate temperature is required for a general semiconductor type gas sensor for the reaction of a sensing material. To do so, a voltage should be applied to a heater. When a sensing material is present in the conventional gas sensor, this should be read as resistance by separately pulling a measurement circuit line, and in this case, four electrodes are needed for the gas sensing element itself. When a structure of these four electrodes is applied, a circuit structure applied to the PCB may become complicated. FIG. 2 shows the four electrodes 130a, 130b, 130c and 130d.

When a fixed resistance or negative temperature coefficient (NTC) thermistor as an output change part D according to the present embodiment is packaged along with the gas sensor by supplementing a resistance value in the same level as that of the sensing material, as illustrated in FIG. 2, only three electrodes 130a, 130b, 130c may be needed. A structure can be simplified upon forming an external module, properties of the sensor can be improved, and reliability can be also increased.

Figure 3:
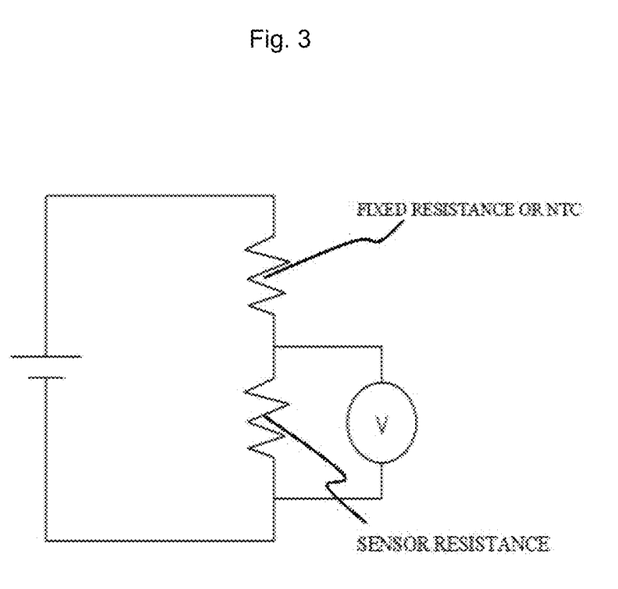
FIG. 3 is a circuit diagram illustrating an output change part according to the embodiment of the present application.

FIG. 3 illustrates a circuit diagram in a case where the fixed resistance or NTC thermistor is included in the output change part D described in FIGS. 1 and 2. The resistance of the gas sensing element and the fixed resistance and NTC (negative temperature coefficient) thermistor may be implemented to be connected in series.

Figure 4:
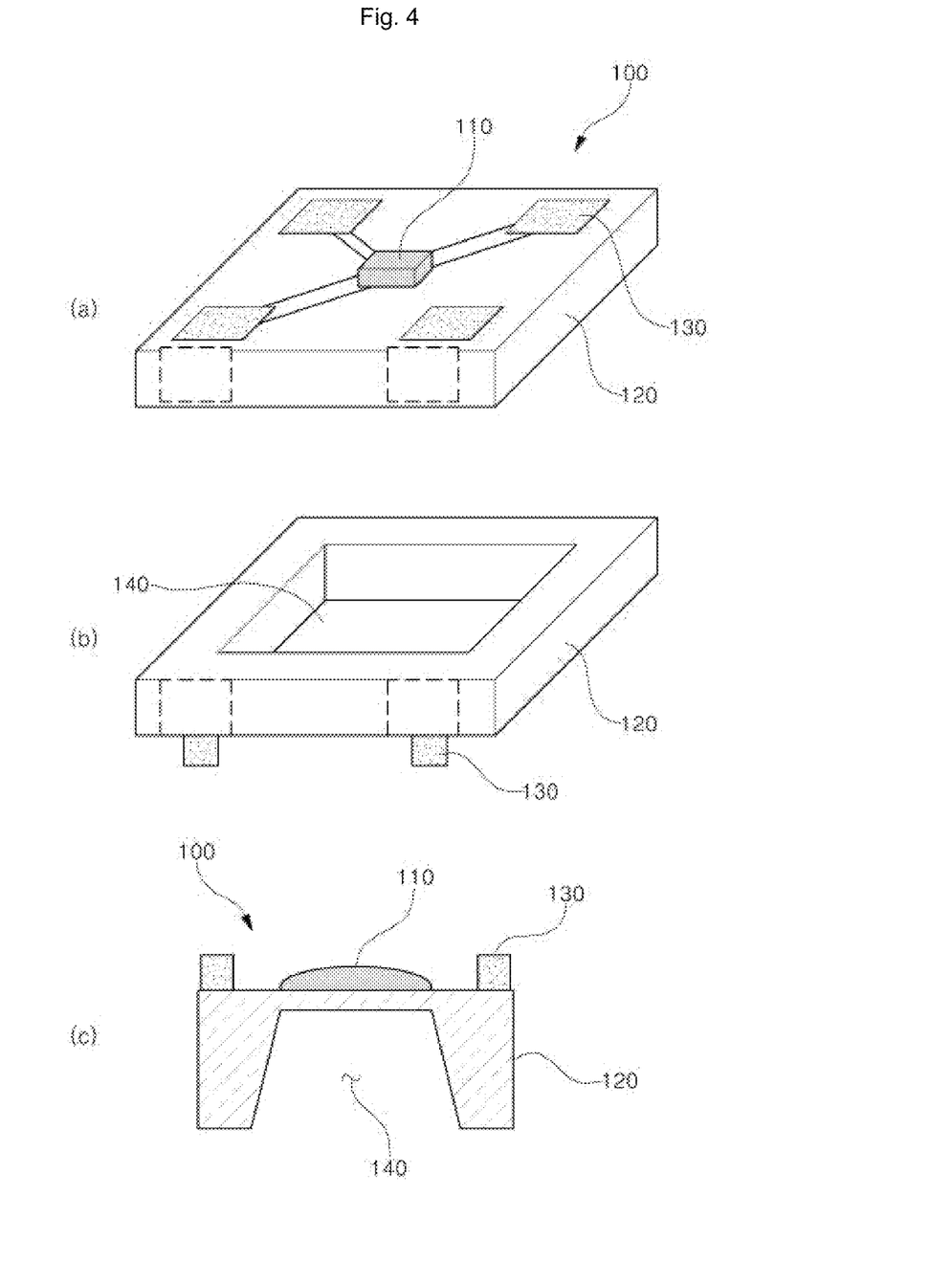
FIG. 4 illustrates a view of a gas sensing element according to according to the embodiment of the present application.

FIG. 4 illustrates an implementation example of the gas sensing element of the present application described in FIGS. 1 and 2. Referring to FIGS. 1 and 4, FIG. 4(a) is a perspective view of the gas sensing element according to the embodiment of the present application, and a gas sensing part 110 for detecting gas via a sensing material or a sensing chip is disposed on a body surface 120. An electrode patterns 130, which are connectable to an external terminal, are provided on an adjacent surface; and the gas sensing part 110 and the electrode patterns 130 are electrically connected to each other.

FIG. 4(b) illustrates a lower surface of the gas sensing element 100 illustrated in FIG. 4(a), and it is more preferable that the lower surface is formed in a structure in which a regular cavity part 140 is formed in the inside of a body 120 so that a gas residence time can be secured. FIG. 4(c) illustrates a sectional view of the gas sensing element. The gas sensing element 100 having the same structure as that of FIG. 2 is mounted on a surface of the first substrate 210 of FIG. 1 so that gas present in a receiving space within the cover module C, in particular, gas flowing via a first movement hole C1 or a second movement hole C2 can be detected.

As illustrated in FIG. 1, according to the embodiment of the present application, the cover module C, disposed in a structure in which an entire upper portion of the gas sensing element 100 and the first substrate 210 are covered in a closely received structure, may be provided. The cover module C has a structure in which an end of the cover module C is closely attached to an edge of the substrate 210 and is provided with a first movement hole C1 and a second movement hole C2, which are gas moving holes for the flow of gas, at an upper portion thereof. The structure of a cap member in a mesh form, which is used in the general gas sensing package, is problematic in that it is difficult to miniaturize it as described above.

According to the embodiment of the present application, the gas moving holes C1, C2 are formed in the upper surface of the integrally formed cover module so that the ventilation of gas can be secured, and a sufficient gas contact space is provided by securing a receiving space in the inside so that gas sensing efficiency can be increased. The first movement hole C1 and the second movement hole C2, which are the gas moving holes, are composed of the first movement hole C1 disposed at a position corresponding to the gas sensing part, and the second movement hole C2 that is spaced apart from the first movement hole and communicates with an inner portion of the cover member. The first movement hole is disposed at the position corresponding to the gas sensing part 110 so that a contact rate with inflow gas can be further increased.

Figure 5:
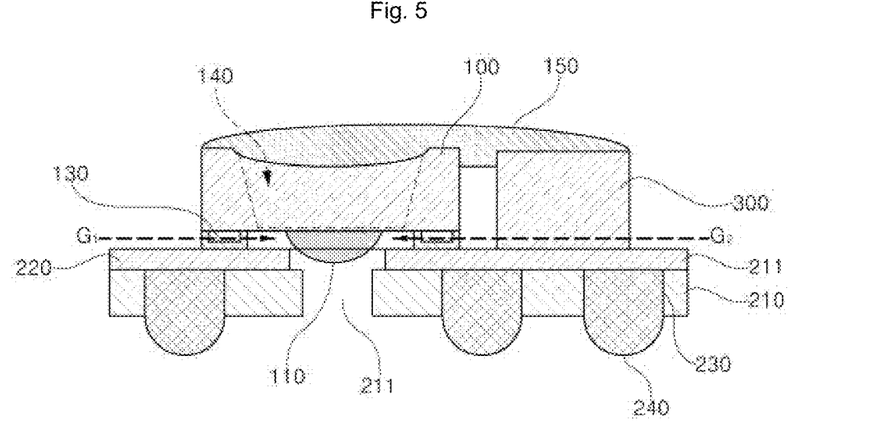
FIGS. 5 and 6 illustrate sectional views of main parts of the gas sensor package according to the embodiment of the present application.
Figure 6:
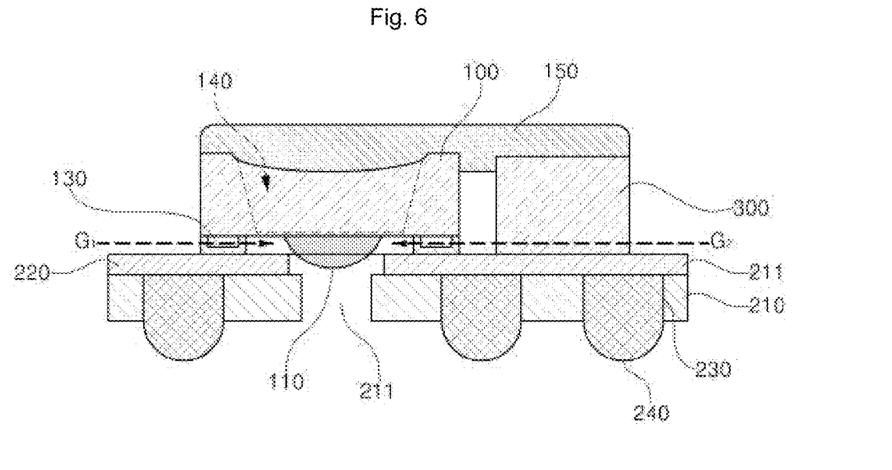

FIGS. 5 and 6 illustrate sectional views of the main parts of gas sensor packages according to the aforesaid embodiment and another embodiment. FIG. 5 shows a case in which a material having a relatively high viscosity is implemented as the cover member. FIG. 6 shows a case in which a material having a low viscosity is implemented as the cover member, thereby showing a difference in shape between the cover members.

The gas sensor package according to the embodiment of the present application includes: the first substrate 210 including the metal patterns 220; the gas sensing element 100 including the gas sensing part 110 disposed to face a surface of the first substrate 210; and gas moving separation parts G1, G2 formed between the gas sensing element 100 and the first substrate 210.

As illustrated in FIG. 5, the first substrate 210 is formed to include the plurality of metal patterns 220 in which electrode patterns (circuit patterns) are patterned on a substrate surface made of an insulating material using a metal material. The first substrate 210 includes a first through hole 211 which is configured to pass through an upper portion and a lower portion of the substrate. The first through hole 211 serves as a path to which the gas sensing part 110 of the gas sensing element 100 is exposed so as to be in contact with gas. In particular, the gas sensing element mounted by bonding of the metal patterns 220 and a bonding pad part 130 of the gas sensing element is separated from the first substrate, namely, forms the gas moving separation parts G1, G2 which become gas moving paths. Due to gas flowing through the gas moving separation parts, more easy detection of the gas can be performed from the gas sensing part 110.

In addition to the first through hole 211, the first substrate 210 has a plurality of second through holes 230 for bonding of the first substrate 210 with an external substrate or object. In particular, as illustrated in FIGS. 5 and 6, the second through holes are filled with a metal material (hereinafter referred to as "a metal filling part 240"), and the metal filling part 240 is formed to partially protrude to a lower portion of the first substrate 210 as illustrated. Such a protruding structure functions to prepare a gas moving path at the same time as enabling electrical connection of an object such as a printed circuit board and the metal filling part 240. This gas moving path may also function to improve gas sensing efficiency by enabling gas to easily flow (which will be described in the section regarding FIG. 9).

In particular, in FIGS. 5 and 6, the gas moving separation parts (G1, G2) look as if a path toward the gas sensing part 110 is blocked, but the drawings illustrate one sectional view, and a bonding portion of the bonding pad part 130 and the metal patterns 220 corresponds to a part. Separation spaces formed by the bonding pad part 130 and the metal patterns 220 are evenly formed along an edge of the gas sensing element 100. Specifically, the metal patterns of an upper surface of the first substrate 210 are directly bonded to the bonding pad part 130 of the gas sensing element 100 or metal electrodes. In general, the metal patterns are formed in a structure in which a plated layer having surface treatment of Ag, Au, Sn and the like is included in a Cu layer, so that a bonding ability with the metal electrodes can be improved. By controlling a thickness of the metal patterns 211, 212, the thickness is formed in a range of 1 µm~several hundreds of µm, thereby functioning to implement a gas moving path which enables gas to be ventilated to a side part of the gas sensing element 100.

The gas sensing element 100 corresponds to a functional part including a sensing material which allows gas sensing. All structures of a gas sensing mode, which are commercialized, may be commonly called the gas sensing element, and a sensing element using an oxide semiconductor, a sensing element using a carbon nanotube, various other sensing semiconductor chips and the like may be applied as the gas sensing element. According to the embodiment of the present application, the gas sensing element 100 is mounted to face a surface of the first substrate 210. A pad part of the gas sensing element 100 and the metal patterns 220 of the first substrate 210 are directly bonded in a flip chip bonding method so that a bonding wire can be removed. An area of the gas sensor package can be reduced, the package can be further miniaturized because a separate cap member or mesh member is not needed to be formed in an upper of the gas sensing part, and a production cost can be reduced.

As illustrated in FIGS. 5 and 6, it may be preferable that the gas sensing part 110 of the gas sensing element 100 be aligned to correspond to the first through hole 211 of the first substrate 210 which may be in contact with gas according to the movement of external gas. It may be the most efficient structure that the gas sensing part 110 is exposed to a gas inlet hole so that contact efficiency with gas can be increased, namely, in light of sensing efficiency, it is most efficient that the gas sensing part 110 and a central portion of the gas inlet hole 211 are disposed to be aligned. The present application is not limited to the structure, and the gas sensing part and the gas inlet hole may be disposed such that the configuration of the align deviates from a predetermined range. In this case, in terms of the gas sensing element according to the embodiment of the present application, gas detection may be supplemented through the gas moving separation parts G1, G2 and the like. The effect of improvement of sensing efficiency may be identically implemented.

In the embodiment of the present application, the gas sensor package may further include one or more adjacent elements 300 which are mounted to the first substrate. These adjacent elements may include active elements or passive elements. As one example, the adjacent elements may further include a fixed resistance or NTC (negative temperature coefficient) thermistor. In the case of the fixed resistance or NTC (negative temperature coefficient) thermistor, the output of a resistance mode is converted into the output of a voltage mode, and in particular, a resistance change value to an initial sensing material according to each temperature is compensated so that a regular initial voltage value can be secured.

In the embodiment of the present application, a cover member 150 configured for simultaneously covering an upper portion of the adjacent elements 300 and the gas sensing element 100 may be provided. The cover member is a special element of the present application and is intended to prepare the cavity part 140 which forms a gas retention region in an inner portion of the gas sensing element 100, and the cover member is also intended to protect the inner portion by covering the upper portion and to control radiant heat. In a case where the upper portion of the adjacent elements 300 and the cover member 150 are fixed together, in addition to protection of the gas sensing element, a bonding ability of the gas sensing element itself can be improved thanks to the fixation with the adjacent elements. In the present embodiment, it is described that the cover member is fixed with the adjacent elements, but various chip package structures (protruding structures except for the gas sensing element) in addition to chip structures such as active elements or passive elements instead of these adjacent elements may be fixed with the cover member.

Various materials having an insulating property may be applied as a material of the cover member 150. For example, as synthetic resin materials, various materials used as sealing materials such as materials including epoxy, urethane and Si may be applied. It may be preferable that materials having a predetermined viscosity be applied as the synthetic resin materials so as not to flow into an inner portion of the cavity part. FIG. 5 shows a case in which a material having a relatively high viscosity is implemented as the cover member, and FIG. 6 shows a case in which a material having a low viscosity is implemented as the cover member, thereby showing a difference in shapes between the respective cover members.

In the case of FIG. 5, when a material of the cover member is epoxy, since the material having a higher viscosity than that of FIG. 6 is used, a curvature is formed at an upper portion of the cover member. The cover member may be also implemented in a structure in which a curvature is also formed at a lower portion thereof, and according to the need, like FIG. 6, by using epoxy having a lower viscosity than that of FIG. 5, the cover member may be implemented in a structure in which the upper portion is flat, thereby enabling the implementation of slimming in size.

Figure 7:
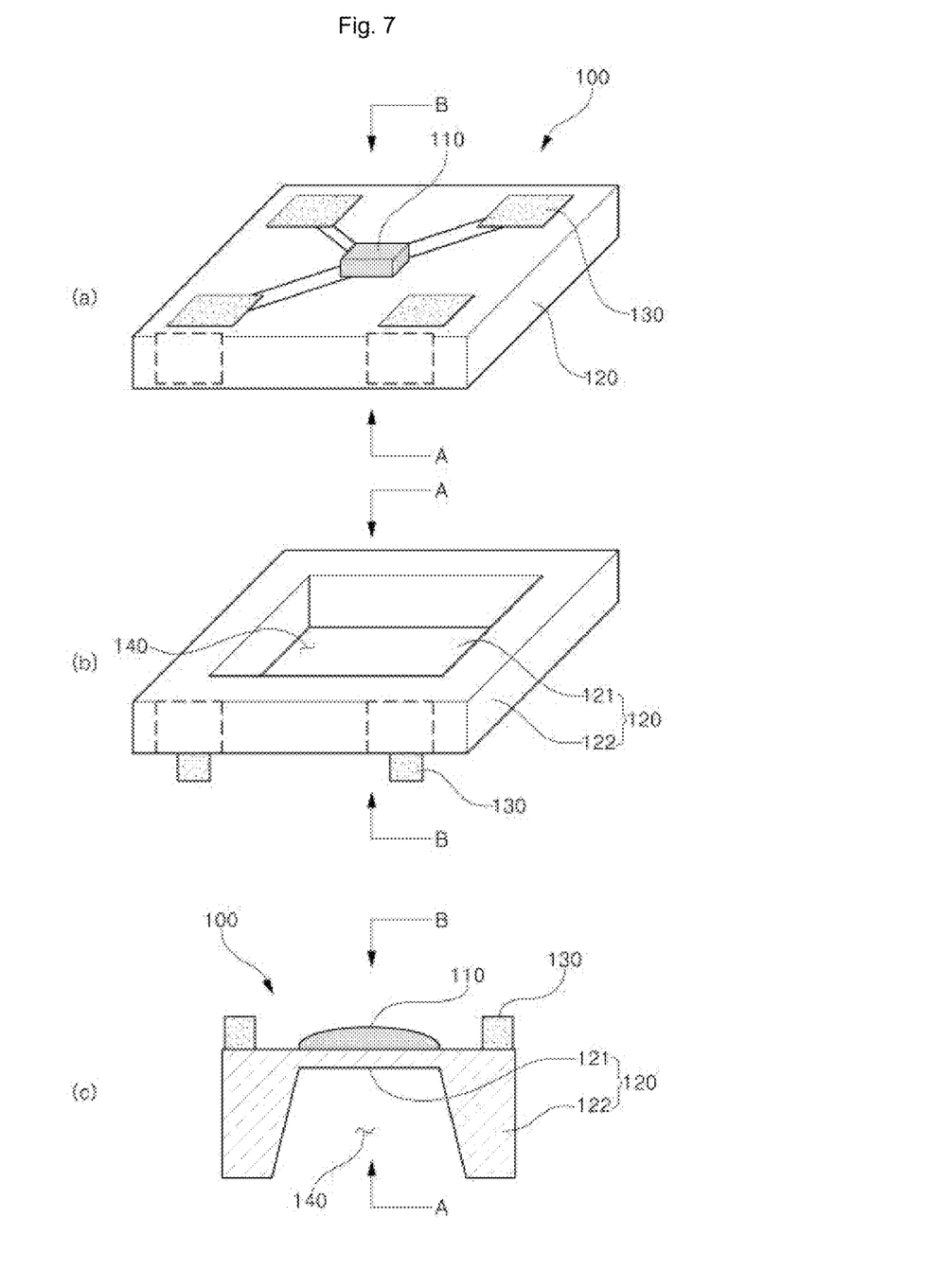
FIG. 7 is a view of the main parts of a gas sensing element according to the embodiment of the present application, the gas sensing element being applied to the gas sensor package described in FIGS. 5 and 6.

FIG. 7 is a view of main parts illustrating a structure of the gas sensing element 100 according to the embodiment of the present application which is applied to the aforesaid gas sensor packages described in the sections regarding FIGS. 5 and 6. The structure of the gas sensing element of FIG. 7 is similar to that of the gas sensing element according to the embodiment described in FIG. 4.

Referring to FIG. 7, the gas sensing element applied to the gas sensor package according to the present embodiment of the invention may include the element body 120 having the cavity part 140 in an inner side by including a lower surface 121 and a side wall 122. A cover member 150 is disposed at an upper portion of the side wall 122 and configured for covering an upper surface of the cavity part 140, and the gas sensing part 110 disposed at an external surface of the lower surface.

FIG. 7(a) defines a lower direction A and an upper direction B of the gas sensing element and is a view of main parts of the gas sensing element as viewed from the upper direction B, FIG. 7(b) is a view of main parts of the gas sensing element as viewed from the lower direction A, and FIG. 7(c) is a sectional view of a side of the gas sensing element.

As shown in FIG. 7(a), the gas sensing part 110 configured for detecting gas via a sensing material or a sensing chip is disposed on the external surface of the lower surface of the element body 120 in the upper direction B is disposed. Electrode patterns 130, which may be connected to an external terminal, are provided at an adjacent surface. The gas sensing part 110 and the electrode patterns 130 are implemented so as to be electrically connected to each other.

As shown in FIG. 7(b), when viewed from the lower direction B of the gas sensing element, the gas sensing element according to the present embodiment is configured such that the side wall 122 and the lower surface 121 are implemented in a structure in which the cavity part 140 is formed in the inner portion of the gas sensing element. With regard to the upper direction, the gas sensing element is provided in a structure in which an open region is implemented.

As shown in FIG. 7(c), when viewed from the lateral section view, the gas sensing element is configured such that the gas sensing part 110 is disposed on an opposite surface of the lower surface 121 of the element body provided with the cavity part 140 in the inner portion. The electrode patterns 130 are provided at the periphery of the gas sensing part so as to be mounted to a substrate and the like later.

Figure 8:
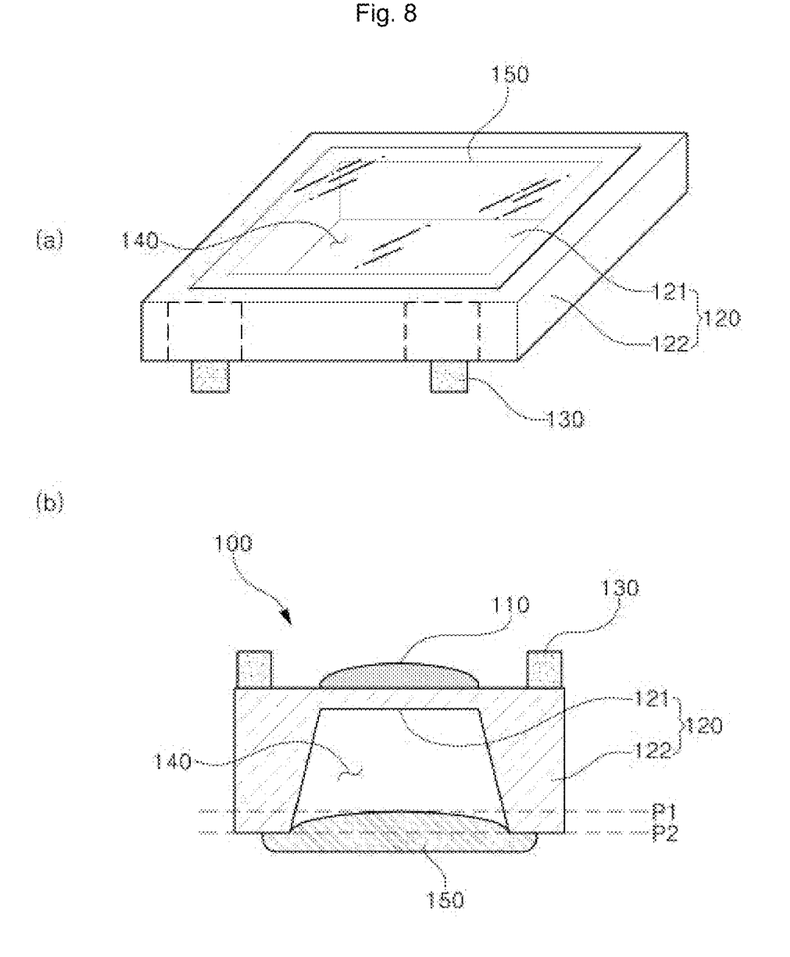
FIG. 8 illustrates a cover member configured for covering an upper surface of a cavity part in a structure of the gas sensing element described in FIG. 7.

FIG. 8 illustrates a cover member 150 configured for covering the upper surface of the cavity part with regard to the aforesaid structure of the gas sensing element. The cover member 150 may be disposed to cover an upper surface of the side wall 122 and an upper surface of the cavity part, and by processing the cover member as a separate structure, the cover member may be implemented such that a synthetic resin film such as polyimide is bonded to the structure.

The cover part may be implemented in a structure in which sealing is performed by dropping a synthetic resin material having a regular viscosity on the upper surface of the cavity part using a dispensing method, so that an inner side of the cavity part and the gas sensing part can be protected. The cover part may be implemented such that a gas retention space for gas sensing is secured in the gas sensing part, and may function to prevent radiant heat. The cover member may be configured to cover the adjacent elements as well as the upper surface of the gas sensing element so that the upper surface of the adjacent elements and the cover member can be simultaneously fixed together, thereby improving a bonding ability of the gas sensing element as described above.

With regard to the configuration of the cover member 150, by dropping a potting material on the upper surface of the gas sensing element and the upper surface of the adjacent elements using a dispensing method and the like, covering of the cover member may be performed. A lower surface P2 of the cover member according to the present embodiment of the invention is configured to be formed smaller than an imaginary horizontal plane P1 formed by an upper end of the side wall 122 of the element body 120. This is intended to form the lower surface of the cover member so as to have a curvature resulting from deflection or surface tension due to the gravity of a synthetic resin material having a regular viscosity.

This structure may function to enable more easy stay and circulation of gas by allowing the upper surface of the cavity part to have the curvature, thereby implementing a supplementary function of improving sensing sensitivity. In order to increase sensing efficiency, minute gas moving holes may be formed on the lower surface of the element body, and the minute gas moving holes may be also additionally implemented in a part of the cover member. The cover member may be implemented not to be in contact with a surface of the first substrate or may be implemented to be in contact with only a part of the surface so that a gas moving separation part formed at a side part of the gas sensing element is not covered.

Figure 9:
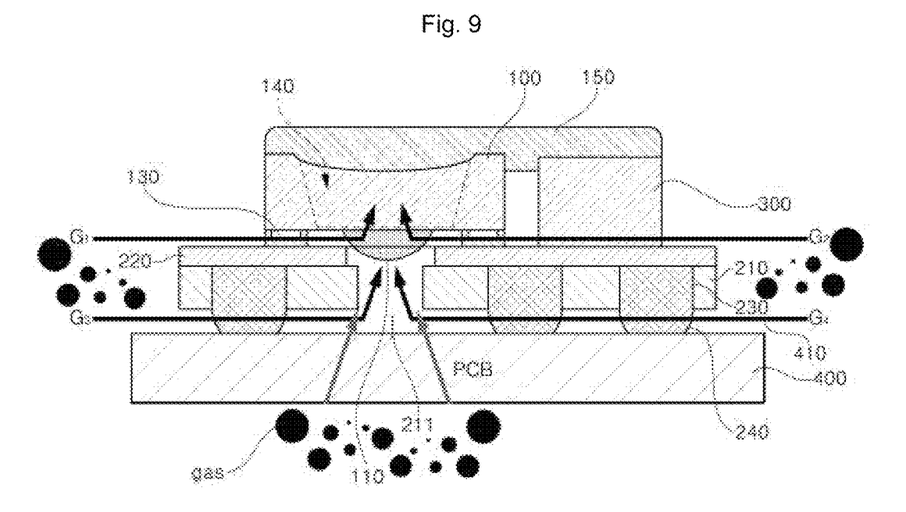
FIG. 9 is view illustrating a structure of a gas sensor package according to another embodiment of the present application.

FIG. 9 is a view illustrating the structure of a gas sensor package according to another embodiment of the present application. The gas sensor package having a structure in which the gas sensing element 100 according to the embodiment of the present application and the first substrate 210 are combined may be implemented to be mounted to the second substrate 400 such as a separate printed circuit board and the like.

The printed circuit board may be applied as the second substrate 400. A flexible material may be applied to the printed circuit board. As illustrated in FIG. 9, the metal filling part 240 of the first substrate 210 and the second substrate 400 which is the printed circuit board are electrically connected to each other. In this case, the metal filling part 240 is configured to partially protrude in the direction of a lower surface of the first substrate 210, and has a predetermined separation part even after being in contact with the second substrate 400. As illustrated, the separation part forms gas moving paths G3, G4 (hereinafter referred to as 'a second gas moving separation part').

The second gas moving separation part 410 enables the gas sensing part 110 to be in direct contact with gas via the first through hole 211 provided at the first substrate in the gas sensor package according to the present embodiment and also enables the gas sensing part to be in contact with gas approaching from a side portion of the gas sensing element, thereby enabling an increase in sensing efficiency.

The gas sensors are generally implemented in a structure in which the gas sensing part is disposed to face an upper surface of the substrate is to secure contact efficiency with gas. Since it may be necessarily configured to face an upper portion of the gas sensing part and a protection net having a mesh structure is needed, a size of the package may be necessarily increased. However, in the case of the package according to the embodiment of the present application, since a portion provided with the gas sensing part is mounted so as to be in contact with the surface of the first substrate, a separate cap is not installed so that the package can be miniaturized and a product cost can be reduced. Furthermore, a gas retention space using the cavity part of the inner portion of the element and a separation part for inducing gas from the first through hole and the side to the gas sensing part are implemented so that sensing efficiency can be also secured.

Figure 10:
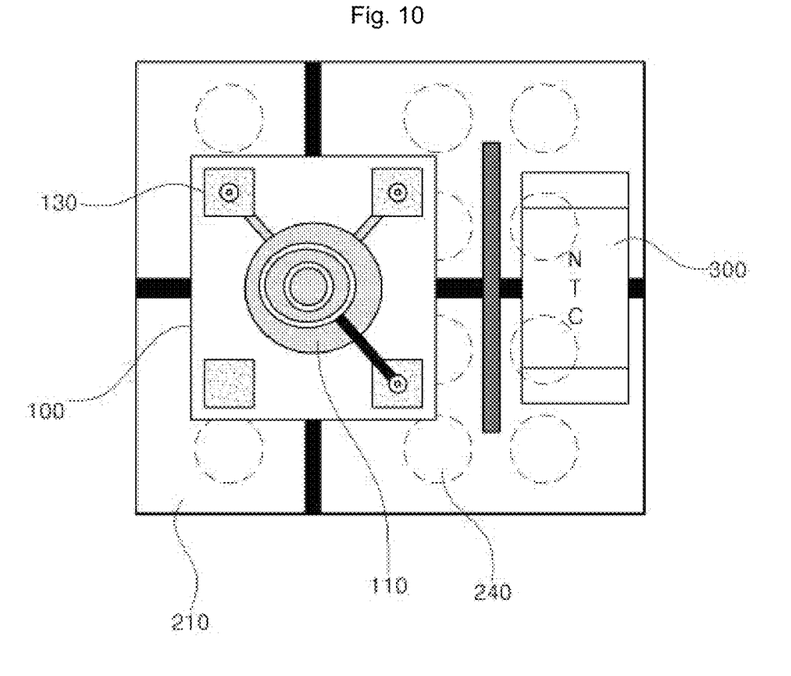
FIG. 10 exemplifies an upper plane view of the structure of the gas sensor packager described in FIG. 9.

FIG. 10 exemplifies an upper plane view of the structure of the gas sensor package described in FIG. 9. The gas sensing part of the gas sensing element is bonded to the surface of the first substrate 100 using a flip chip method so that they can face each other, and the metal filling part 240 is disposed at a lower portion. A fixed resistance or an NTC (negative temperature coefficient) thermistor 300 may be added (for brief illustration, illustration for the configuration of the cover member is omitted).

Figure 11:
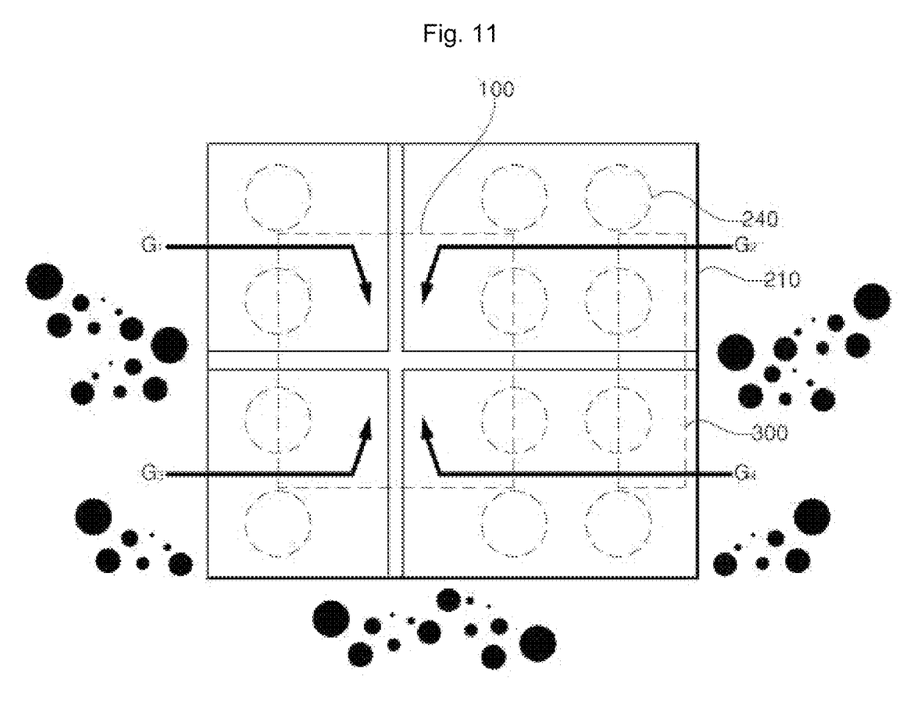
FIG. 11 is a planar view of the gas sensor package of FIG. 10 as viewed from the above.

FIG. 11 is a view of a plane for the gas sensor package of FIGS. 9 and 10 as viewed from above, and illustrates gas moving paths G3, G4 of gas via the second gas moving separation part after a lower PCB and the first substrate 210 have been bonded. As illustrate in FIG. 11, the gas flowing from the side of the gas sensing element 100 is transferred through the gas moving separation part G1, G2, and from left and right side parts, the gas is smoothly ventilated via the second gas moving separation part G3, G4 between the first substrate and the second substrate so that the gas can be transmitted to the gas sensing part.

As set forth above, according to some embodiments of the present application, since the output change part is provided in the gas sensor package including a gas sensor, a resistance output mode can be converted into a voltage output mode, and thus an initial resistance change value to the sensing material can be compensated, thereby enabling a regular initial voltage value to be secured.

Also, according to some embodiments of the present application, in a structure in which the gas sensing element is mounted on the substrate using a flip chip bonding method, the gas moving separation part is provided between the substrate and the gas sensing element so that gas sensing efficiency can be maximized by inducing smooth gas movement.

In particular, since the cover member is implemented on an upper surface of the element body so that the cavity part can be formed in the gas sensing element, the element including the gas sensing part can be protected. Meanwhile, the cover member is fixed to the upper portion of the adjacent elements being present in the periphery of the gas sensing element so that a bonding ability of the elements and the substrate can be reinforced.

Moreover, when gas sensing is performed by applying the gas sensing element according to the embodiment of the present application, gas can be stayed in the cavity part, thereby increasing sensing efficiency. In addition, the through holes are provided in the first substrate combined as the package so that inflow or outflow of the gas can be performed via the through holes, thereby enabling gas sensing and increasing sensing efficiency. Also, the gas sensor having a slim structure can be formed.

In particular, since the gas sensing element is directly mounted to the metal electrodes of the substrate, it is advantageous in that there is no need to perform wire bonding; an area of the package can be reduced; and an entire height of the package can be reduced.

Also, since a separate cap, that protects the gas sensing part of an upper portion of a sensor chip and is necessarily needed for the conventional gas sensor package, is not needed, a product cost can be reduced and the package can be further miniaturized than the existing package.

Moreover, with regard to gas paths for gas sensing, in addition to primary inflow of the gas via the gas inlet holes of the substrate, since inflow of the gas via the separation part of the side of the chip is performed, it is also advantageous in that effective sensing can be implemented.

The gas sensor package according to various embodiments of the present application may be applied to general IT devices from a reduction in entire size of the gas sensor package and a reduction in product cost by implementing the slim structure and multifunction.

As previously described, in the detailed description of the invention, having described the detailed exemplary embodiments of the invention, it should be apparent that modifications and variations can be made by persons skilled without deviating from the spirit or scope of the invention. Therefore, it is to be understood that the foregoing is illustrative of the present application and is not to be construed as limited to the specific embodiments disclosed, and that modifications to the disclosed embodiments, as well as other embodiments, are intended to be included within the scope of the appended claims and their equivalents.

The present application has been made keeping in mind the above problems occurring in the related art. An aspect of the present application provides a gas sensor package which is configured such that an output change part is provided in the gas sensor package including a gas sensor so that a resistance output mode can be changed to a voltage output mode, thereby enabling the gas sensor to have a regular initial voltage value by compensating a resistance change value to an initial gas sensing material.

Also, another aspect of the present application provides a gas sensor package which is configured such that a gas moving path is formed between a gas sensing element and a substrate in order to increase gas sensing efficiency so that a sensing rate of gas can be increased, and a cover member is implemented in an upper portion of a body of the gas sensing element so as to be fixed with adjacent elements of the periphery of the gas sensing element, thereby increasing the reliability of fixation.

According to an aspect of the present application, there is provided a gas sensor package including: a substrate including a plurality of metal patterns; a gas sensing element mounted to the substrate; and an output change part mounted to the substrate and configured for changing an output mode of the gas sensing element.

Also, according to another aspect of the present application, there is provided a gas sensor package including: a first substrate including metal patterns; a gas sensing element including a gas sensing part disposed to face a surface of the first substrate; and a gas moving separation part formed between the gas sensing element and the first substrate. Furthermore, the gas sensor package further includes a cover member configured for covering an upper surface of a cavity part, and in particular, the cover member is implemented to be closely attached to an upper portion of at least one or more adjacent elements.

It will also be understood that when an element is referred to as being "on" another element, substrate, layer (film), region, pad or patterns, it can be directly on the other element or substrate, or intervening elements may also be present. Further, it will be understood that when an element is referred to as being "under" another element, substrate, layer (film), region, pad or patterns, it can be directly under, or one or more intervening elements may also be present.

Any reference in this specification to "one embodiment," "an embodiment," "example embodiment," etc., means that a particular feature, structure, or characteristic described in connection with the embodiment is included in at least one embodiment of the invention. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A gas sensor package, comprising:
   a first substrate including metal patterns; and
   a gas sensing element mounted to the first substrate,
   wherein the gas sensing element includes:
      a body having a cavity part configured for accommodating gas at an upper portion of the body;
      a bonding pattern disposed on a lower surface of the body, and the bonding pattern connected to the metal patterns;
      a gas sensing part disposed on the body and configured to communicate with the cavity part and including a gas sensing material; and
      a cover member configured to cover an upper surface of the cavity part and an upper surface of the body,
   wherein the gas sensing part is face to face with a top surface of the first substrate,
   wherein a first through hole is provided in the first substrate to align in a vertical line with the gas sensing part;
   wherein the gas sensing part is exposed through the first through hole,
   wherein the first through hole has a width that is smaller than a width of the gas sensing part,
   wherein the cover member includes:
      a first portion disposed on the upper surface of the body, and
      a second portion disposed on the upper surface of the cavity part, and having a flat upper surface and a curved lower surface, and
      wherein the lower surface of the second portion is positioned at a lower level than the upper surface of the body.

2. The gas sensor package of claim 1, further comprising an output change part mounted to the first substrate and configured for changing an output mode of the gas sensing element.

3. The gas sensor package of claim 2, wherein the output change part comprises a fixed resistance or NTC (negative temperature coefficient) thermistor electrically connected to the gas sensing element.

4. The gas sensor package of claim 3, wherein the output change part is configured such that resistance of the gas sensing element and the fixed resistance or NTC (negative temperature coefficient) thermistor are connected in series.

5. The gas sensor package of claim 3, wherein the gas sensing material of the gas sensing part has substantially the same resistance change ratio for each temperature as that of the NTC thermistor.

6. The gas sensor package of claim 5, wherein the gas sensing material is composed of any one oxide selected among Sn, Zn, Ti, W and Ir.

7. The gas sensor package of claim 1, wherein a gas moving separation part for the movement of gas is provided between the first substrate and the gas sensing element.

8. The gas sensor package of claim 1, wherein the cover member is in contact with an upper portion of at least one or more adjacent elements that are adjacent to the gas sensing element.

9. The gas sensor package of claim 1, wherein the cover member is not in contact with a surface of the first substrate.

10. The gas sensor package of claim 1, wherein the first substrate includes a second through hole that passes through a lower surface of the first substrate on which the metal patterns are formed.

11. The gas sensor package of claim 10, further comprising a metal filling part filled into the second through hole.

12. The gas sensor package of claim 11, wherein the metal filling part is configured to further protrude than a lower surface of the first substrate.

13. The gas sensor package of claim 1, wherein the first substrate includes:
   a second through hole that passes through a lower surface of the first substrate on which the metal patterns are formed, and
   a metal filling part provided within the second through hole to connect with a second substrate and provided with a gas moving path between the first substrate and the second substrate, wherein the metal filling part is configured to protrude further than a lower surface of the first substrate.

14. The gas sensor package of claim 1, wherein the gas sensing element comprises first to fourth electrodes connected to the gas sensing part.

* * * * *